United States Patent
Kullberg

(10) Patent No.: US 6,733,727 B1
(45) Date of Patent: May 11, 2004

(54) CONDENSATION INDUCED WATER HAMMER DRIVEN STERILIZATION

(75) Inventor: Craig M. Kullberg, Idaho Falls, ID (US)

(73) Assignee: Bechtel BWXT Idaho, LLC, Idaho Falls, ID (US)

(*) Notice: Subject to any disclaimer, the term of this patent is extended or adjusted under 35 U.S.C. 154(b) by 0 days.

(21) Appl. No.: 09/719,890
(22) PCT Filed: Jun. 29, 1999
(86) PCT No.: PCT/US99/14760
§ 371 (c)(1), (2), (4) Date: Dec. 19, 2000
(87) PCT Pub. No.: WO00/01255
PCT Pub. Date: Jan. 13, 2000

Related U.S. Application Data

(60) Provisional application No. 60/091,341, filed on Jul. 1, 1998.

(51) Int. Cl.[7] ................................. A61L 2/00
(52) U.S. Cl. .................. 422/20; 422/127; 422/128
(58) Field of Search ................. 422/20, 127, 128

(56) References Cited

FOREIGN PATENT DOCUMENTS

| EP | 0 0780 056 A1 | * | 6/1997 |
| EP | 0 800 775 A1 | * | 10/1997 |

* cited by examiner

Primary Examiner—Krisanne M. Thornton
(74) Attorney, Agent, or Firm—Trask Britt PC

(57) ABSTRACT

A method and apparatus (10) for treating a fluid or materials therein with acoustic energy has a vessel (14) for receiving the fluid with inner walls shaped to focus acoustic energy to a target zone within the vessel. One or more nozzles (26) are directed into the vessel (14) for injecting a condensable vapor, such as steam, into the vessel (14). The system may include a steam source (18) for providing steam as the condensable vapor from an industrial waste heat source. Steam drums (88) are disposed between the steam source (18) and nozzles (26) to equalize and distribute the vapor pressure. A cooling source (30) provides a secondary fluid for maintaining the liquid in the vessel (14) in subcooled conditions. A heating jacket (32) surrounds the vessel (14) to heat the walls of the vessel (14) and prevent biological growth thereon. A pressurizer (33) may operate the system at elevated pressures.

36 Claims, 8 Drawing Sheets

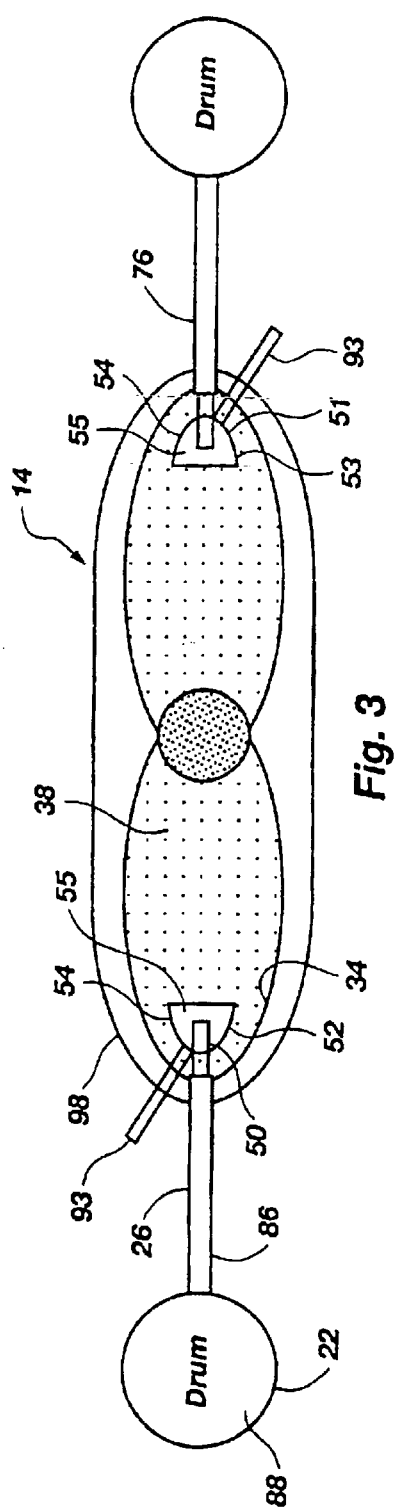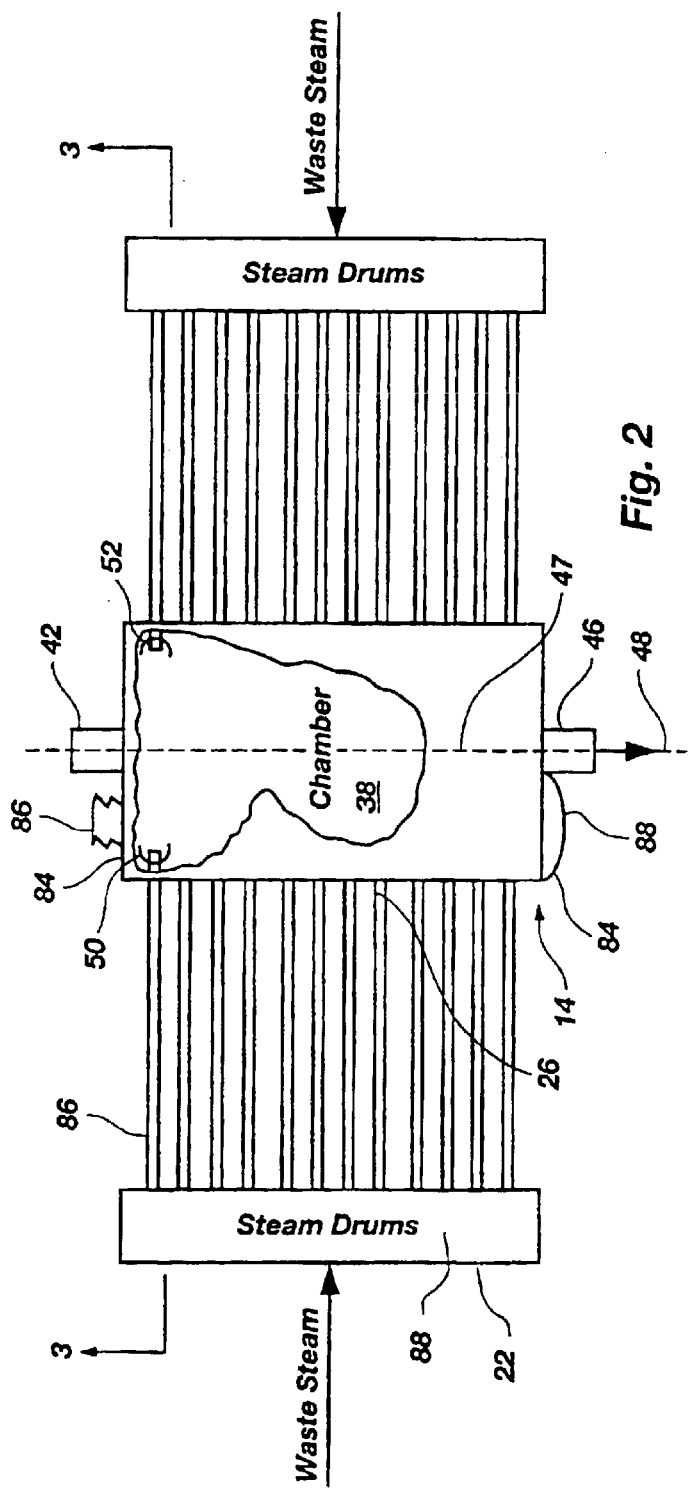

us 6,733,727 B1

CONDENSATION INDUCED WATER HAMMER DRIVEN STERILIZATION

RELATED APPLICATION

This application claims priority to PCT application S/N PCT\US99\14760, filed Jun. 29, 1999 and provisional application S/N 60/091,341, filed Jul. 1, 1998.

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

BACKGROUND OF THE INVENTION

1. Field of the Invention

The present invention relates generally to a method and apparatus for treating a fluid, such as the sterilization of water, or a material therein using acoustic energy in the form of cavitation, large amplitude acoustic waves, and/or water hammer, generated by the rapid condensation of steam which is injected into the fluid. More particularly, it concerns a method and apparatus for selectively injecting steam into a reflector member disposed in the fluid which is shaped to focus and direct the acoustic energy at a target zone within the chamber where the acoustic waves converge causing secondary cavitation, the chamber also being shaped to focus the acoustic energy.

2. Background Art

A growing number of municipalities both inside and outside the United States are constrained to using drinking water supplies that come from local rivers, lakes, and reservoirs that contain significant amounts of hazardous micro-organismns. In many cases conventional chemical detoxification methods result in undesirable amounts of chlorine and chlorine byproducts in the treated water. Consequently, the municipal drinking water supply is characterized by water that is unpalatable as well as being a potential health problem. In recent years various non-chemical sonication schemes have been devised to replace or limit the use of chemicals in water treatment procedures.

These sonication schemes utilize high-amplitude ultrasonic sound waves to cause cavitation in a liquid. Cavitation occurs when the high-amplitude ultrasonic sound waves create gas-bubble cavities in the liquid. When the cavities collapse they produce intense localized pressures. This cavitation may be induced to destroy liquid-borne organisms, mix fluids or slurries, promote certain chemical reactions, and otherwise treat fluids or materials therein.

The high-amplitude ultrasonic sound waves are typically generated by electrically driven piezoelectric or magnetostrictive transducers. The transducers are usually directed into a static liquid tank or a tank in which the liquid is circulated in order to sterilize objects within the tank, such as surgical instruments, or to sterilize the fluid itself One disadvantage of transducers is that they are typically confined to small scale systems or batch processes.

Some larger scale systems for processing a continuous flow of water have been proposed. For example, U.S. Pat. No. 5,611,993, issued Mar. 18, 1997, to Babaev, discloses a method which uses various tank configurations and inlet and outlet locations to cause temporary pooling of the water while a transducer for transmitting a high frequency sound wave is directed at the pooled water. U.S. Pat. No. 4,086, 057, issued Apr. 25, 1978, to Everett, discloses a free jet of water directed against an ultrasonic vibrating surface. One disadvantage with these systems is that they are not practical for large scale disinfection of a continuously flowing fluid. U.S. Pat. No. 5,611,993, issued Mar. 18, 1997, to Babaev, discloses a plurality of opposing transducers. One disadvantage with some of these systems is their use of a larger number of transducers which consequently utilize a larger amount of electricity to operate.

Other systems require additional processing steps to supplement the sonic process. For example, U.S. Pat. No. 5,466,425, issued Nov. 14, 1995, to Adams discloses a system utilizing an applied voltage, ultraviolet radiation, and high frequency. Similarly, U.S. Pat. No. 5,326,468, issued Jul. 5, 1994, to Cox, discloses cavitation induced by the pressure drop across a nozzle throat and subsequent ultraviolet radiation, ion exchange, and degassifying treatment. See also U.S. Pat. No. 5,494,585, issued Feb. 27, 1996, to Cox; and U.S. Pat. No. 5,393,417, issued Feb. 28, 1995, to Cox. One disadvantage of these systems is their reliance on secondary treatments. Another disadvantage is their continued use of trstems utilize a cavitation chamber. For example, U.S. Pat. No. 5,519,670, issued May 21, 1996, to Walter, discloses a cavitation chamber in which acoustic pulses are generated by repeatedly closing a valve, creating water hammer. The water hammer propagates into the cavitation chamber through a diaphragm. See also U.S. Pat. No. 5,508,975, issued Apr. 16, 1996, to Walter. One problem with this type of system is that repeatedly closing the valve fatigues the system components. Another problem with this type of system is the use of a diaphragm which may become fatigued and fail. Another problem with many systems is the complexity and number of components subject to failure.

Another problem with many of the above systems is that the acoustic energy generated is inefficiently used. For example, the acoustic energy is indirectly propagated from a pipe system into a cavitation chamber. Other systems merely direct the transducer in the desired direction. U.S. Pat. No. 5,459,699, issued Oct. 17, 1995, to Walter, discloses a flexible, indented pipe to direct some of the water hammer in the pipe into a surrounding fluid. Most of the acoustic energy in these systems randomly propagates through the system.

Although most systems utilize transducers to create cavitation, some systems utilize the pressure drop across a nozzle to induce cavitation downstream of the nozzle throat. See U.S. Pat. Nos. 5,326, 468; 5,494,585; and 5,393,417. Traditionally, this type of cavitation sometimes occurs naturally in fluid systems and is generally considered undesirable as it contributes to the fatigue and failure of system components.

In addition to micro-organisms, some fluids or fluid systems also have difficulty with larger organisms. For example, the intake canals of power plants are clogged by zebra mussels. These intake canals typically contain large volumes of water, and conventional chemical treatments can prove to be expensive or environmentally unfriendly.

Furthermore, cavitation is also known to be useful in other processes in addition to sterilization of fluids. Cavitation may also be used to sterilize other materials or objects in the fluid; promote chemical reactions (sono-chemistry); treat wood fibers for paper pulp production; de-gas liquids; mix chemicals or slurries; or break down certain compounds.

Therefore, it would be advantageous to develop a method and apparatus capable of sterilizing a large amount of continuously flowing water suitable for use with municipal water supplies, industrial waste water, or utility water supplies. It would also be advantageous to develop such a method and apparatus which utilizes a novel acoustic source rather than traditional transducers. It would also be advantageous to develop such a method and apparatus that is simple and has fewer components. It would also be advantageous to develop such a method and apparatus which efficiently utilizes the acoustic energy. It would also be advantageous to develop a method and apparatus capable of handling larger organisms.

OBJECTS AND SUMMARY OF THE INVENTION

It is therefore an object of the present invention to provide a method and apparatus for sterilizing a large amount of continuously flowing water suitable for use with municipal water supplies, municipal waste water, and industrial food processing waste water.

It is another object of the present invention to provide such a method and apparatus for treating other fluids and/or materials and objects in the fluid; promoting chemical reactions; treating wood fibers for paper pulp production; de-gassing liquids; mixing chemicals or slurries; and breaking down certain compounds.

It is another object of the present invention to provide such a method and apparatus which utilizes a less expensive acoustic source, rather than traditional transducers.

It is another object of the present invention to provide such a method and apparatus which is simple; has few moving parts; and has fewer components and is easily serviceable.

It is another object of the present invention to provide such a method and apparatus which efficiently utilizes the acoustic energy.

It is another object of the present invention to provide a method and apparatus capable of handling larger organisms.

The above objects and others not specifically recited are realized in a number of specific illustrative embodiments of an apparatus and system for treating a fluid and/or materials therein with acoustic energy. For example, the apparatus of the present invention is particularly well suited for sterilizing a continuous flow of water having microorganisms therein by destroying the micro-organisms with induced cavitation. The system includes a vessel for receiving the fluid; a source of condensable vapor, such as steam; vapor headers for equalizing vapor pressure and protecting against liquid backflow; a directional nozzle array for focusing and/or directing acoustic energy; a source of cooling fluid for maintaining subcooled conditions in the vessel; an optional pressurizer or surge tank to either control pressure surges or operation at elevated pressures. The pressurizer option will be dictated by the engineering applications that are involved. Also, for biological applications, an optional heating jacket will be employed to sufficiently heat the vessel walls to retard the growth of organisms which may become attached to the walls.

The vessel has an inner wall defining a chamber. The chamber is configured to allow the fluid to pass therethrough in a continuous stream. The walls of the of the chamber are shaped or curved to focus and/or direct acoustic energy to a particular area of the chamber defining a target zone. The vessel may be elongated and formed of various elongated portions coupled together. The portions may have various cross sectional shapes for focusing the acoustic energy to the common target area. For example, the chamber may be formed by a plurality of portions having partially elliptical cross sections, each with a separate, outer focal point, and a common, inner focal point disposed in the target zone. The vessel may be elongated or create an elongated fluid path to create long enough dwell times such that the target products, such as micro organisms, spend enough time in the acoustic target zone to be destroyed.

The nozzle array has one or more nozzles or spargers coupled to the vessel and directed into the chamber. The nozzle array also has one or more reflector members or shells. The reflector members have a curved wall defining an indentation for focusing and/or directing acoustic energy. The reflector members may have one or a cluster of nozzles directed into the cavity. The indentations or cavities may be parabolic or circular shapes. An individual nozzle cluster and its immediate reflecting shell define a single acoustic source. The shells may have leakage paths, or apertures formed therein, which allow cooling water to circulate about the cavity and maintain subcooled conditions inside the shell.

The nozzles are configured for injecting a condensable vapor into the curved indentations of the reflector members, and thus into the vessel. For example, the nozzle may be a steam sparger injecting steam. The acoustic energy is created by the rapid condensation of the vapor in the presence of the fluid. The acoustic energy is generated by localized water hammer shock waves as vapor bubbles implode. These localized shocks will evolve into large amplitude acoustic pulses that will be focused on the target, or directed at the target zone. Additional acoustic energy may also be induced by local turbulence and mechanical loading on the nozzle and reflector members. This acoustic energy is focused and/or directed at the target zone by the reflector members, and by the inner surfaces of the chamber. The acoustic waves converge with one another in the target zone inducing cavitation. The induced cavitation may be used to treat the fluid or materials therein. The source of the condensable vapor is preferably a steam source supplying waste steam from a utility plant.

Each acoustic source, or steam sparger which its reflector member, is supplied by process steam via thermally insulated steam lines. These steam lines are in turn connected to one or more common steam headers. For most applications, the steam flow in each line will be modulated using off the shelf technology. This modulation can be accomplished with hydraulic valves that area partially opened and closed in a periodic manner. Self modulation schemes may also be employed and will be discussed latersteam lines and associated check valves will be employed to control accidental liquid backflow. The vapor headers equalize the vapor pressure to the various nozzles. In addition, the headers act as a shock absorber in the event of backflow of liquid into the steam pipe.

The cooling system circulates a cooling fluid through the vessel to maintain the vessel, or fluid to be treated, in subcooled conditions. Cooling of the main cavity and the spargers will be done with either pumped bulk flow across the main cavity, or the cooling fluid may be locally injected into the shell cavity of each acoustic source, or a combination of these methods. The coolant may be the same as the fluid which is treated.

For biological applications, the heating jacket surrounds the vessel and heats the walls of the vessel. The jacket may be a secondary, outer shell disposed around the vessel, or it may be a pipe coiled about the vessel. The heating jacket keeps the walls heated to prevent biological growth thereon.

There are several possible geometric configurations for the resonance chamber which house the above mentioned array of acoustic sources, which include but are not limited to cylindrical, spherical, and toridal configurations. The acoustic arrays will focus sonic energy in a target zone of the cavity, where intense cavitation is induced. The cavity walls will help focus this energy by reflecting scattered sound waves that are not directly absorbed in the target region. This target zone will either have no contact or minimal contact with the resonance chamber to minimize cavitation induced wall erosion. Resonate modes that are excited in the cavity will also help to enhance cavitation in the target zone. However, there will be cases where unwanted resonate modes impinge directly on the cavity walls and are too intense. In these situations, baffles will be used to scatter sonic energy to limit localized wall cavitation erosion.

In addition, one or more individual acoustic sources described above can be used for stand alone applications. Each sparger, or nozzle cluster, encased inside its reflecting shell along with its insulated process steam supply line and cooling water intake line, if needed, can be placed in some pre-existing hydraulic structure like an intake canal to power plant or water treatment facility. As an example, the stand alone acoustic source or sources could be used to destroy organisms that clog the intake filters to these facilities.

Finally, for specialized applications that are primarily non-biological, the cavitation chamber can be adapted to operate at elevated pressures with the use of off the shelf pressurizer technology If the in flowing and out flowing liquid to the chamber is isolated form the open atmosphere, and the system is connected to a pressurizer, it is possible to increase the ambient chamber pressure by several hundred atmospheres. An added benefit of using a pressurizer (even at low pressure) is that this system absorbs large amplitude pressure pulses that may otherwise cause pipe and/or vessel ruptures. At elevated pressures, the attendant increase in cavitation implosion energy can increase aby as much as two orders of magnitude.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which:

FIG. 2 is a top view of a fluid treatment apparatus in accordance with the principles of the present invention;

FIG. 3 is a side, cross-sectional view of the fluid treatment apparatus of FIG. 2, taken along section 3—3;

FIG. 7a is a side view of an alternative embodiment of a fluid treatment apparatus in accordance with the principles of the present invention;

FIG. 8b is an end view of the fluid treatment apparatus of FIG. 8a;

FIG. 9b is an end view of the fluid treatment apparatus of FIG. 9a;

DETAILED DESCRIPTION

Figure 1:
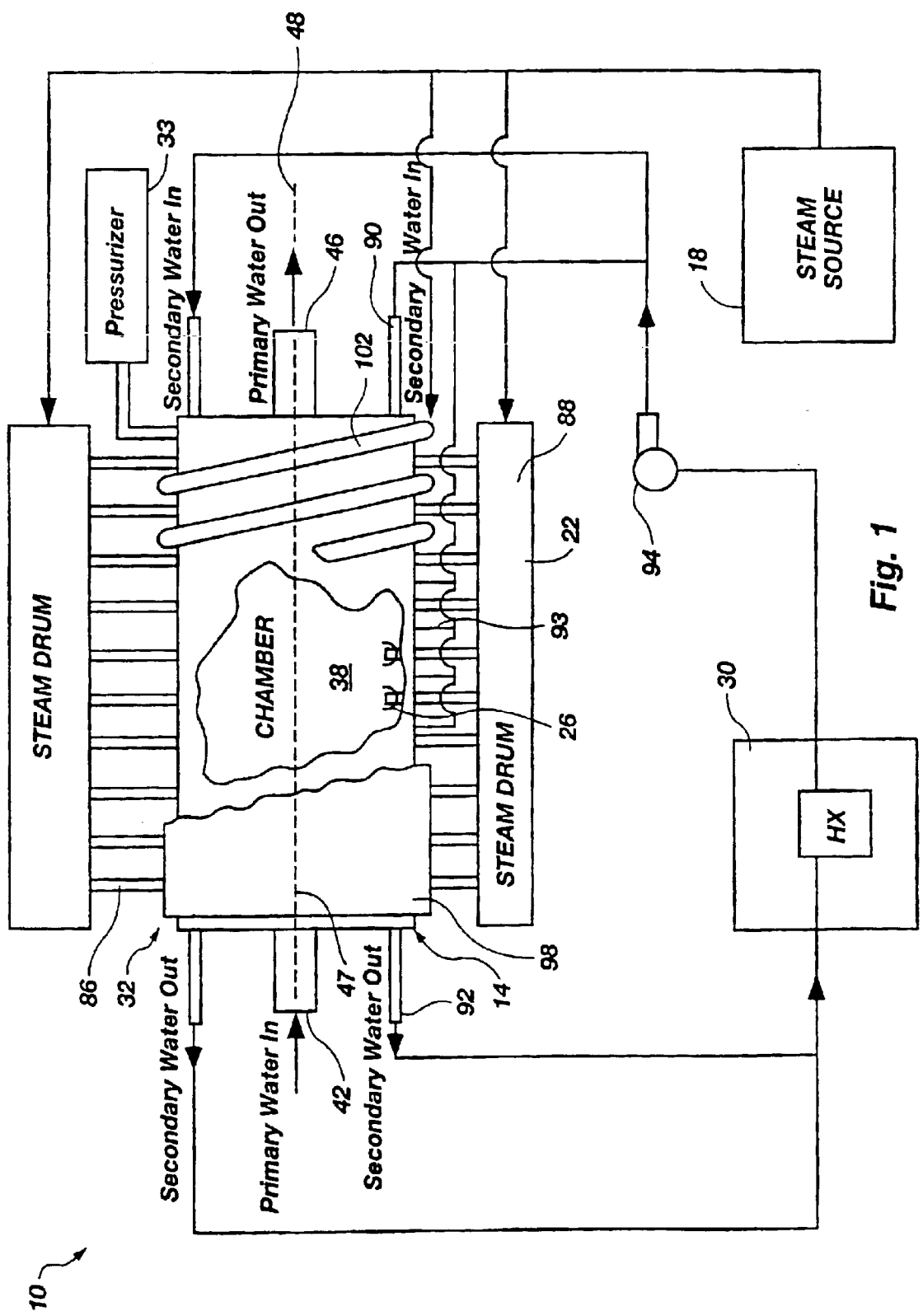
FIG. 1 is a schematic view of a continuous fluid sterilization system in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Referring to FIG. 1, a fluid treatment system or apparatus, indicated generally at 10, of the present invention is shown for treating a fluid and/or materials or objects in the fluid with acoustic energy. The system 10 is described and illustrated with respect to a specific embodiment for sterilizing a continuous flow of water having micro-organisms therein, such as a municipal water system. It is of course understood that the system of the present invention may also be used for treating other fluids and/or materials therein. For example, the system may be used for promoting chemical reactions; treating wood fibers for paper pulp production; de-gassing liquids; mixing chemicals or slurries; and breaking down certain compounds.

In addition, the term "acoustic energy," as used herein, refers to and is intended to encompass various related or similar acoustic events given various terms, such as ultra-sonic radiation, acoustic waves, water hammer, cavitation, etc. For example, ultra-sonic radiation usually refers to high frequency wave energy or vibrations which propagate through a given medium at the speed of sound for that medium. Such ultra-sonic waves or vibrations usually have a frequency greater than the audible range, or greater than about 10–15 kHz. Water hammer usually refers to a high pressure pulse created when a rapidly flowing stream of fluid in a conduit is suddenly blocked. The kinetic energy of the flowing fluid is converted to a high pressure pulse. Cavitation occurs in a liquid when the pressure at some point in the system is reduced to the vapor pressure of the liquid. Under such conditions, vapor bubble cavities form and then collapse. When each vapor cavity implodes, intense localized pressure is generated that can be in the GPa range. Subsequent vapor cavity collapse generates acoustic disturbances with a frequency spectrum that may have both ultra-sonic and sonic frequency components. Also, for sufficient acoustic energy intensities, cavitation may be induced by a broad range of frequencies that include both sonic anc ultra-sonic ranges.

The system or apparatus 10 has a fluid vessel 14 for receiving a fluid; a condensable vapor source or vapor supply system 18 for providing or producing a condensable vapor; vapor headers 22 for equalizing vapor pressure and protecting against liquid backflow; a directional nozzle array 26 or acoustic source for focusing or directing acoustic energy; a source of cooling fluid or a cooling system 30 for maintaining subcooled conditions in the vessel; a heating jacket 32 for heating the walls of the vessel; and a pressurizer 33, all of which will be described in greater detail below. The cooling source 30, heating jacket 32, and pressurizer 33 are optional and their use will be dictated by the particular application and associated operating conditions.

The fluid vessel 14 is configured for receiving a fluid, such as water containing microorganisms. The vessel 14 has an inner surface 34, as shown in FIG. 3, defining a fluid chamber 38. The vessel 14 also has a primary inlet 42 for allowing fluid to enter into the chamber 38 and a primary outlet 46 for allowing fluid to exit the chamber 38. Baffles may be placed at the vessel inlet to enhance turbulent mixing in the vessel.

The vessel 14 and chamber 38 are preferably elongated to allow for extended dwell times of the fluid and/or materials therein to maximize the probability for cavitation exposure for a typical parcel of liquid entering the cavity. Thus, the flow of fluid defines a continuous and elongated fluid path 47 through the chamber 38 between the inlet 42 and the outlet 46 and generally parallel and coaxial with a longitudinal axis 48 of the chamber 38. It should be pointed out that the inlet 42 and outlet 46 are not necessarily coaxial. Depending on other relevant key design hydraulic parameters, such as Reynolds numbers and boundary conditions, the inlet 42 and outlet 26 may be off set from the central axis of the chamber 38 to ensure more complete turbulent mixing. For off set designs, the flow path would not coincide with a target zone described below. In addition, the vessel 14 and chamber 38 are preferably sized to allow a large volume of fluid to flow therethrough. Thus, the system may be scaled to supply purified water for various sized urban populations. Alternatively, the vessel 14 or chamber 38 may be configured or shaped in various different ways as discussed more fully below.

The directional nozzle array 26 has a plurality of single acoustic sources. Referring to FIG. 3, the nozzle array 26 advantageously has one or more nozzles or spargers, such as a first nozzle or sparger 50 and a second nozzle or sparger 51, for injecting a condensable vapor, such as steam, into the chamber 38. The nozzles 50 and 51 are coupled to the vessel 14 and directed into the chamber 38.

The nozzle array also advantageously includes first reflector member 52 and second reflector member 53, coupled to the one or more nozzles or spargers, such as the first and second spargers 50 and 51, and disposed in the chamber 38. The reflector members 52 and 53 have a curved wall 54 defining an open indentation or cavity 55. The reflector members 52 and 53 are disposed in the chamber 38 and thus in the fluid so that the fluid is received within the cavities 55. The curved indentations 55 surround the nozzles or spargers 50 and 51. The spargers 50 and 51 are directed into the open cavities 55 such that the condensable vapor is injected into the open cavities 55. The curved wall 54 is shaped to focus and/or direct the acoustic energy created by the condensing vapor to a particular zone within the chamber 38 defining a target or kill zone 56.

A single nozzle 50 or 51 may be directed into each reflector member 52 or 53, or a cluster of nozzles may be directed into each reflector member. Each reflector member and nozzle, or cluster of nozzles, defines a single acoustic source. The nozzle array 26 includes a plurality of these single acoustic sources, or nozzles/reflector members. The nozzle array 26 may be located along a side or sides of the vessel 14 or chamber 38 and include a string of nozzles 50 and 51 with reflector members 52 and 53 along the length of the chamber 38, as shown in FIGS. 1 and 3.

The injection of the condensable vapor into a liquid environment results in an almost immediate localized bubble collapse with an attendant release of intense acoustic energy. The injection of the condensable vapor is modulated. The reason for modulating the injection is two fold. First, the modulation allows continuous replacement of subcooled water in a cavitation zone near the steam nozzle outlets. Second, the modulation allows for impulsive loading that augments the excitation of normal modes in the cavity, or optionally near specially designed metal structures that are designed to oscillate at high frequencies. For example, the acoustic energy may be used to kill or destroy microorganisms in water, thus sterilizing the water.

Figure 4:
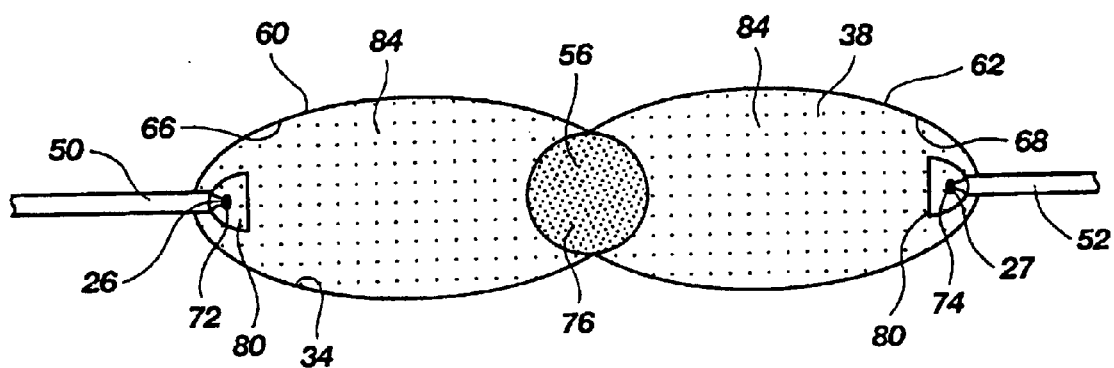
FIG. 4 is a schematic view of the fluid treatment apparatus of FIG. 2.

Referring to FIG. 4, the inner surface 34 of the chamber 38 is preferably shaped to focus and/or direct the acoustic energy in the chamber 38 to the target zone 56. The elliptical surface 34 of the chamber 38 is designed to enhance the focusing of the acoustic energy that has not been directly absorbed in the target zone 56. The inner surface 34 of the chamber 38 preferably forms at least two parallel, adjoining portions, such as a first portion 60 and a second portion 62. Thus, the two portions 60 and 62 define the fluid channel 38 with the target zone 56 between the two portions 60 and 62. Each portion 60 and 62 has an inner surface 66 and 68 which forms a curve to focus and/or direct the acoustic energy at the target zone 56. Thus, the inner surface 34 of the chamber 38 has at least two curved portions 60 and 62 which are shaped to focus the acoustic energy to the target zone 56.

The injection of the condensable vapor into a liquid environment results in an almost immediate localized bubble collapse with an attendant release of intense acoustic energy. The injection of the condensable vapor is modulated. The reason for modulating the injection is two fold. First, the modulation allows continuous replacement of subcooled water in a cavitation zone near the steam nozzle outlets. Second, the modulation allows for impulsive loading that augments the excitation of normal modes in the cavity, or optionally near specially designed metal structures that are designed to oscillate at high frequencies. For example, the acoustic energy may be used to kill or destroy microorganisms in water, thus sterilizing the water. The curved inner surface 66 and 68 of each of the two portions 60 and 62 of the chamber 38 preferably form an ellipse, or are elliptical. Thus, the chamber 38 is formed by two elongated portions 60 and 62 having elliptical cross sections coupled together. The first portion 60 has a first outer focal point 72 and the second portion 62 has a second outer focal point 74. In addition, each portion 60 and 62 has another focal point 76 located in a common area, namely the target zone 56. Thus, each portion 60 and 62 has two focal points including an inner focal point 76 in the target zone and an outer focal point 72 and 74. The inner focal points 76 are located near the center or middle of the chamber 38 while the outer focal points 72 and 74 are located near the outside or circumference of the chamber 38. The focal points are preferably defined by the focal points of the elliptical cross-sections of the adjoining portions. The focal points of the elliptical cross-sections are also focal axes of the elongated, cylindrical, elliptical chamber 38.

The nozzle array. 26 defines a first nozzle array and generates acoustic energy along the first elliptical focal axis 72 in the chamber 38. The first nozzle array 26 is a plurality of the first nozzles 50 and first reflector members 52. A second nozzle array 27, symmetrical with the first array 26, generates acoustic energy along the second elliptical focal axis 74. The second nozzle array 27 is a plurality of the second nozzles 51 and second reflector members 53. The first and second focal axes 72 and 74 define first and second axial source locations which are separate from one another and separate from the target zone. Thus, acoustic energy created at the first and second focal points 72 and 74 is directed and focused to the common second focal point 76 or target zone 56. Secondary cavitation is caused as the acoustic waves converge with one another in the target zone 56. Thus, the target zone 56 is also a cavitation zone. The secondary cavitation and acoustic energy may be used to destroy or kill micro-organisms within water.

The chamber 38 geometry can be employed to support resonate cavity modes and to focus acoustic pressure waves. Induced cavity normal acoustic modes can either enhance or degrade system performance depending on the particular type of modes generated. Pressure waves created by the rapid condensation of the vapor as it contacts the fluid propagate through the chamber. The shape of the inner surface 34 of the chamber 38 directs and/or focuses the pressure waves so that cavitation occurs as the pressure waves converge with one another. Thus, it is desirable to create, direct, and focus the waves or acoustic energy at a common area, such as the target zone 56, where cavitation may be used to destroy micro-organisms, or otherwise treat the fluid or material therein. The primary acoustic waves intersect directly at the common focal point or target zone. The secondary acoustic waves bounce off the cavity walls and are combined at the common focal point or target zone.

The vessel 14 also has end plates 84 disposed on both ends of the vessel 14 with baffles 86 coupled thereto to scatter and absorb unwanted resonate axial wave modes that do not pass directly through the target zone, as shown in FIG. 2. Depending on the circumstances, end plate baffle covering may be partial or complete. These axial wave modes may induce unwanted cavitation outside of the intended cavitation zone that can defocus energy aimed at the target zone and induce cavitation wall erosion. An alternative scheme for suppressing axial cavity modes is to redesign the axial geometry of the resonating chamber such that flat end plates are replaced with hemispherical end caps 88, as shown in FIG. 2. On the other hand, induced damped radial cavity modes directed between the first and second focal points 72 and 74 and that converge on the central target zone 56 are desirable and enhance system operation if absorption in the target zone keeps acoustic intensities low at the opposite right and left ends of the cavity 38, so as to avoid wall cavitation erosion bounded by the transmission zone 84.

Referring to FIGS. 1 and 2, the directional nozzle arrays 26 and 27 are configured with a cluster of nozzles or spargers 50 and 51 surrounded by reflector members 52 and 53. The nozzle arrays 26 and 27 are directed at the axial source locations 72 and 74 which extending along the length of the vessel 14 and chamber 38. The acoustic energy from these source locations 72 and 74 propogate through the transmission zone 84 and converge at plurality of target zones 56 that extend along the length of the chamber 38. The fluid flow path 47 extends along the longitudinal axis 48 of the chamber 38, and is generally within or coaxial with the target zone 56. Thus, as the fluid passes through the chamber 56, it may be exposed at various and multiple locations to multiple or continuous applications of acoustic energy and cavitation.

Referring to FIGS. 1–3, a header 22 is coupled to the nozzle array 26, or the nozzles or spargers 50 and 52, process lines 86 for communicating the vapor from the header 22 to the nozzles 50 and 52. The process lines 86 are preferably straight, or free of elbows and the like, to prevent water hammer damage. The header 22 is a pressurized cylindrical drum having a cavity 88 formed therein for receiving the vapor. The header 22 equalizes pressure to each supply line 86. In addition, the header also serves as a shock absorption reservoir to dissipate pressure waves that are generated when flow through the supply lines is modulated or for accidental liquid backflow. Check valves may be located in each supply line to limit damage caused by accidental liquid backflow.

The vessel 14 also has a secondary inlet 90 for allowing a cooling fluid to enter into the chamber 38 and a secondary outlet 92 for allowing cooling fluid to exit the chamber 38. The cooling fluid helps maintain subcooling conditions in the chamber 38. The cooling fluid may be the same as the fluid to be treated, such as water. In addition, the cooling fluid may or may not be separated from the fluid to be treated. A pipe, not shown, may extend between the secondary inlet and secondary outlet so that the cooling fluid does not mix with the fluid to be treated. In addition, the nozzle arrays may be cooled by a distribution of branching cooling lines 93 that individually inject cooling water into the vicinity of each nozzle 50 and 52. The secondary inlet 90 receives the cooling fluid from a source of cooling fluid 30. The cooling fluid may be pumped from the source 30 to the vessel 14 by a pump 94.

The cooling fluid and source 30 form a cooling system for removing thermal energy deposited in the vessel 14 from the vapor, which may be heated. The cooling system maintains uniform subcooling conditions in the chamber 38 or the transmission zone 84. The pump 94 circulates the cooling fluid to ensure that local bulk temperature cond 52 are maintained in a subcooled state. The source of cooling fluid 30 may include heat exchangers in a cooling pond. Cooling also occurs as a consequence of the passage of the fluid to be treated through the chamber 38.

The heating jacket 32 is disposed about at least a portion of the vessel 14. The heating jacket heats the vessel 14, or the vessel's walls, to prevent the growth of biological substances thereon. It will be appreciated that the existence of micro-organisms in the fluid, and thus the vessel, in combination with the heat from the steam may facilitate the growth of these biological substances on the walls of the vessel. Thus, the heating jacket heats the walls of the vessel to a temperature in which the biological substances may not grow. The heating jacket 32 may be a secondary vessel or shell 98 formed about the vessel 14 through which a heated fluid may be circulated about the vessel 14, as shown on the left hand side of the vessel in FIG. 1 and in FIG. 3. Alternatively, the heating jacket 32 may be a pipe 102 coiled about the vessel 14 through which a heated fluid is circulated, as shown on the right hand side of the vessel in FIG. 1. The heated fluid may be steam and supplied with the same process steam used to power the acoustic sources.

In the preferred embodiment, the apparatus or system 10 is configured to sterilize a continuous stream of water containing micro-organisms. Thus, a constant flow of water is passed through the vessel 14 and chamber 38. The water is preferably pre-treated before entering the chamber so that it is subcooled, de-aerated, and pre-filtered.

The chamber 38 is sized to meet the purified water requirements of a given location. For example, the chamber 38 may be sized to supply purified water to hundreds of thousands of people. For the example, a population of one hundred thousand people whose nominal daily consumption is 100 gallons per person per day is assumed. (This is a figure of merit for estimated world wide consumption. Actual U.S. consumption is approximately 180 gallons per person per day.) Thus, the base line per-day treatment capacity for the system is about $10^7$ gallons (or $3.75 \times 10^4$ m$^3$). The acoustic energy loads needed to completely sterilize a cubic meter of water is estimated to be on the order of about $5 \times 10^5$ J/m$^3$. Thus, the acoustic daily time average power loads of at least $2.17 \times 10^5$ watts are needed to service drinking water for a population of $10^5$ people. It should be noted that energy requirements for boiling an equivalent amount of liquid is several orders of magnitude higher relative to acoustic sterilization. In addition, volumetric flow rates are on the order of 1 m$^3$/sec (16,000 gpm). For this example, the target zone has a cross sectional area of approximately 1 m$^2$. The length of the target zone, and thus the vessel, is approximately 50 m. The ambient operating pressure is maintained between 1 and 3 atmospheres. At one atmosphere, the cavitation power threshold is about 3000 w/m$^2$. For 100% absorption in the target zone, this gives a total energy absorption rate on the order of 0.5 MW or energy densities on the order of $10^4$ watts/m$^3$. For a 1 m$^3$ (264 gallons) parcel of liquid to transit the absorption zone moving at 1 m/s, this results in deposition rates on the order of 0.5 MJ for 50 sec dwell times in the kill zone. Actual net residency time in the cavity itself is longer because of turbulent motion. Therefore, the vessel and chamber are sized for the commercial sterilization of a municipal water supply.

In addition, for such a system the source of condensable vapor 18 is a steam source, and the header 22 is a steam drum. The steam source 18 preferably utilizes waste heat from a conventional power plant, such as conventional open cycle gas turbine plants, to generate steam. Other possible waste heat sources include industrial waste treatment facilities that employ plasma torch technologies to dispose of large quantities of solid wastes.

The cooling system may use counter current external cooling loops driven by pumps. The pumps may be one or more steam turbine high capacity centrifugal pumps driven by part of the waste process steam feed from the steam headers. Without local subcooling, acoustical energy conversions to be less efficient. In addition, uncontrolled heat-ups in the nozzle region may increase local vapor pressure making it easier to cavitate liquid in the surrounding transmission zone. Unwanted cavitation in the transmission zone will de-focus and absorb energy that is intended for the absorption zone.

Therefore, such a system will limit the use of chlorine and other chemicals to disinfect water relative to large scale municipal water treatment methods. The results include safer and more palatable drinking water. In addition, such a system utilizes a less expensive source of acoustic energy. Preferably using industrial waste heat to generate steam. Furthermore, such a system efficiently utilizes the acoustic energy by focusing or directing it towards the target zone.

It is of course understood that the above described system, and the configured chamber, may be used to treat other fluids or materials therein. For example, the above system or chamber may be used for promoting chemical reactions; treating wood fibers for paper pulp production; de-gassing liquids; mixing chemicals or slurries; breaking down certain compounds; and destruction of biological munitions.

More exotic and problematic applications include operating the cavitation chamber at high or ultra high pressures with the use of a pressurizer 33 and state of the art structural and materials engineering technologies. These systems may also have to operate in extremely hot or cold temperature environments. Cavitation implosions can focus energy by as much as 12 orders of magnitude. Also, cavitation induced implosions in an elevated pressure environment may be sufficient to locally heat material to induce either fusion or fission reactions. Thus, when current structural technology becomes capable of accommodating such elevated operating pressures or severe temperature conditions it may be possible to use cavitation technology to sustain a break-even nuclear exothermic reaction that is practical to generate useful energy. Liquids deployed in such a device could include heavy water, cryogenic liquids, mixtures of deuterium and tritium, or molten metals containing fissile elements.

In addition, it is understood that the above described chamber may be configured in various different ways to focus and/or direct the acoustic energy in an efficient manner, some of which are described below.

Figure 5:
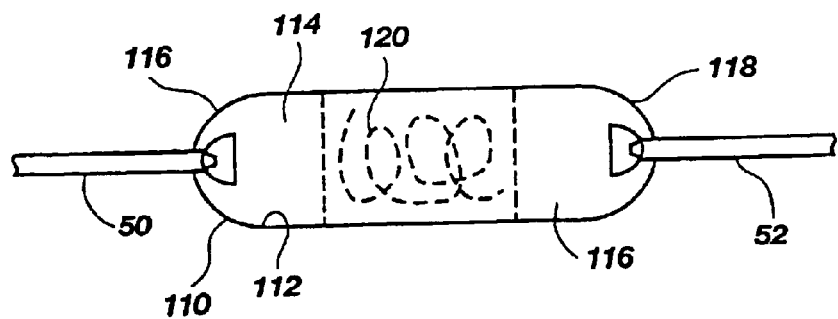
FIG. 5 is schematic view of an alternative embodiment of a fluid treatment apparatus in accordance with the principles of the present invention.

Referring to FIG. 5, an alternative embodiment of a vessel 110 is shown with an inner surface 112 defining a chamber 114 having two opposing portions 116 and 118 with curved cross sections. The curved portions 116 and 118 direct acoustical energy created by the injection of a condensable vapor from the nozzles 50 and 52 to a target zone 120.

Figure 6:
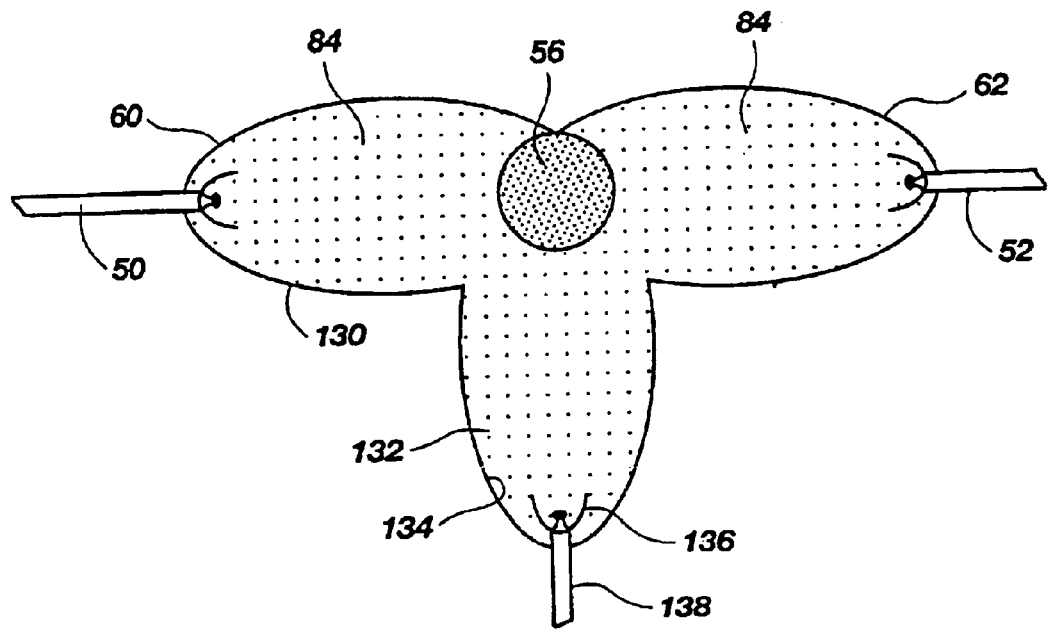
FIG. 6 is schematic view of an alternative embodiment of a fluid treatment apparatus in accordance with the principles of the present invention.

Referring to FIG. 6, an alternative embodiment of a vessel 130 is shown which is similar to the embodiment of FIG. 3, but has a third elongated portion 132. The third portion 132 is parallel with and coupled to the first and second portions 60 and 62. The third portion 132 may be perpendicular to the first and second portions 60 and 62, as shown, or all three portions may be configured with equal angular spacing therebetween. The third portion 132 preferably has a curved inner surface 134 with a parabolic cross section. Thus, the third portion 132 has a third outer focal point 136 and another focal point in common with the first and second portion located in the target zone 56.

In addition, a third nozzle 138 is directed to inject a condensable fluid at the third focal point. Therefore, the acoustic energy generated from the injection of a condensible fluid from three separate points is directed and focused at the target zone. A generalization of the above scheme can be extended to an arbitrary number of overlapping cylindrical elliptical cavities that share a common focal point which form a flower pedal or lotus like pattern.

Figure 7:
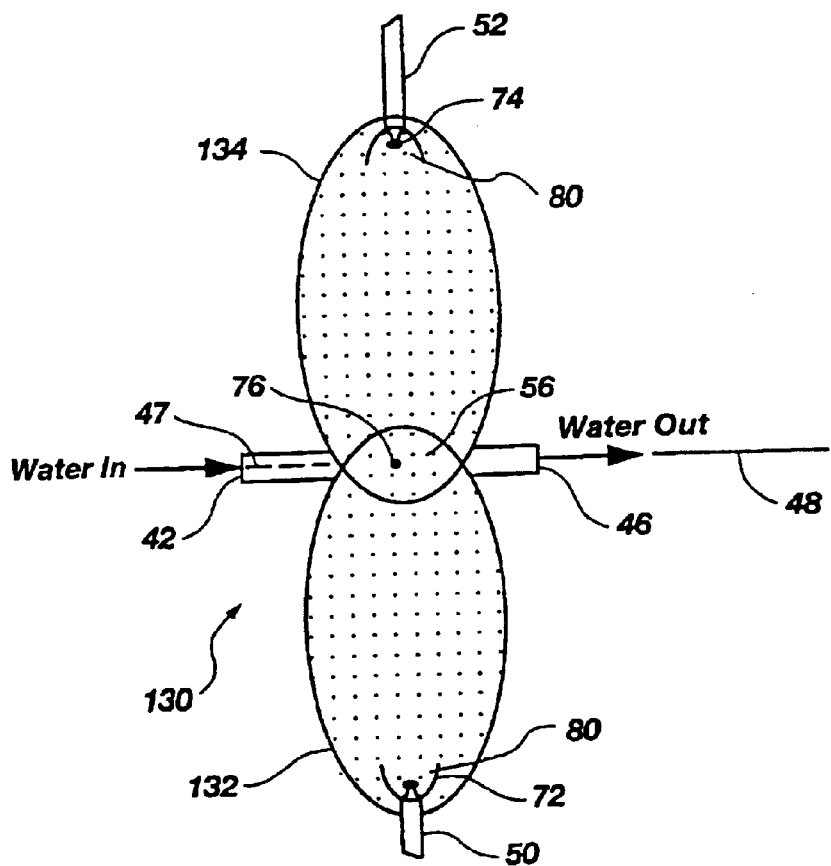
FIG. 7 is schematic view of an alternative embodiment of a fluid treatment apparatus in accordance with the principles of the present invention.

Referring to FIG. 7, an alternative embodiment of an apparatus 130 is shown in which the vessel 14 has two portions 132 and 134 of elliptical cross section that share a common inner focal point, as in FIG. 4, but instead are volumes bounded by surfaces of revolution about the axly by surfaces of revolution about the axis connecting the source locations 72 and 74. The two portions 132 and 134 may be non-elliptical. In addition, multiple nested sets of these portions sharing a common focal point may be generated. For the case of surface of revolution about the outer focal points 70 and 72, an identical overlapping set of portions that is perpendicular to the page may be added to again generate a lotus like patterned cross section. In this example, acoustic energy will be focused from the multiple portions to a common target zone.

Figure 8A:
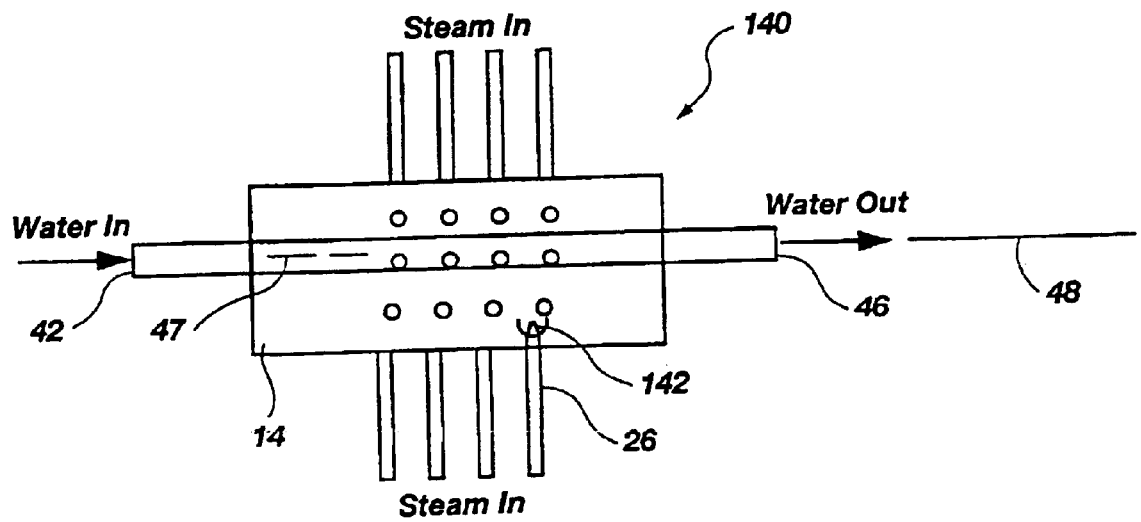
Figure 8B:
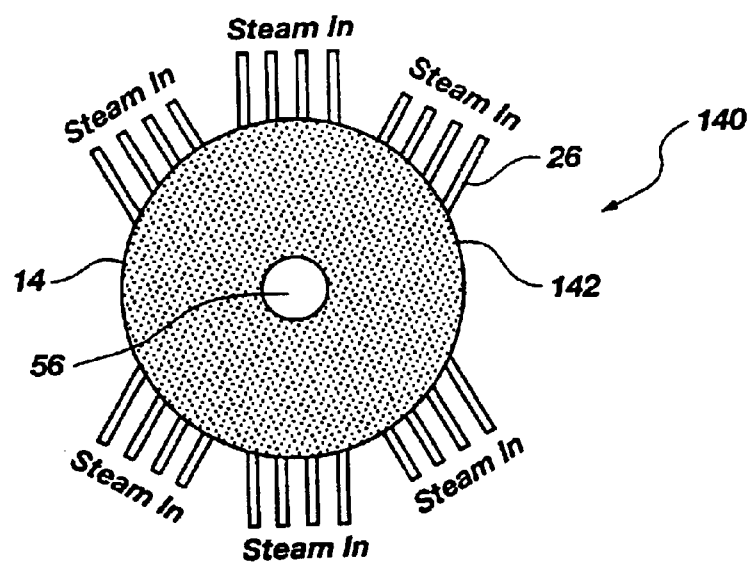

Referring to FIGS. 8a and 8b, an apparatus 140 has a vessel 14 with an inner surface forming an elongated cylinder. A plurality of acoustic sources 142, or nozzle arrays 26, are disposed along the length of the cylinder, as shown in FIG. 8a, and about the circumference of the cylinder, as shown in FIG. 8b. The acoustic sources 142 have nozzles directed to inject the condensable vapor into the cylinder. Because multiple acoustic sources 142 are disposed about the circumference of the cylinder, the acoustic energy created by the rapid condensation of the vapor will converge towards the center of the cylinder, or longitudinal axis of the vessel 48 as shown in FIG. 8a, defining a target zone 56 generally extending the length of the cylinder and coaxial with the longitudinal axis. The acoustic energy may also propagate throughout the cylinder. It is of course understood that the cylinder may have a cross sectional shape that is right circular, or may have some other shape, such as elliptical, etc.

Figure 9A:
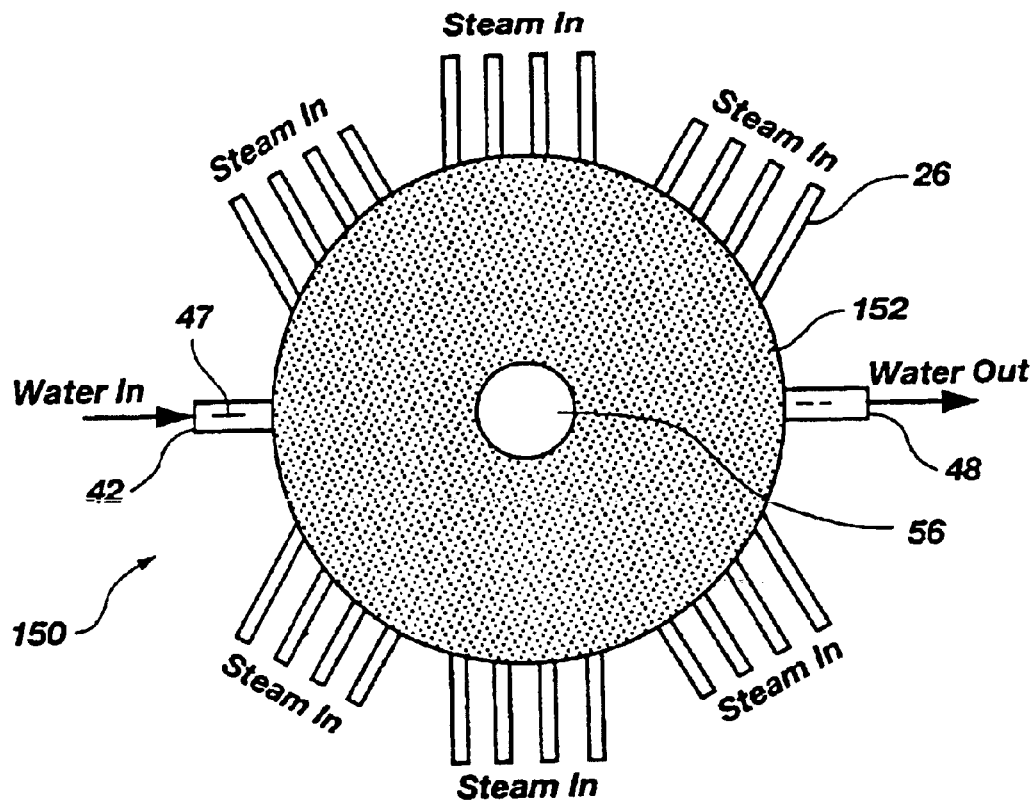
FIG. 9a is side view of an alternative embodiment of a fluid treatment apparatus in accordance with the principles of the present invention.
Figure 9B:
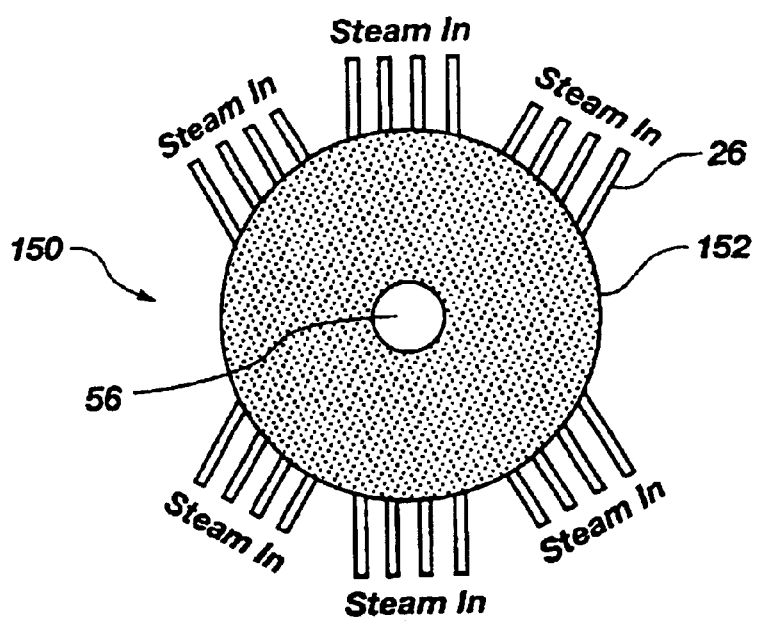
Figure 10:
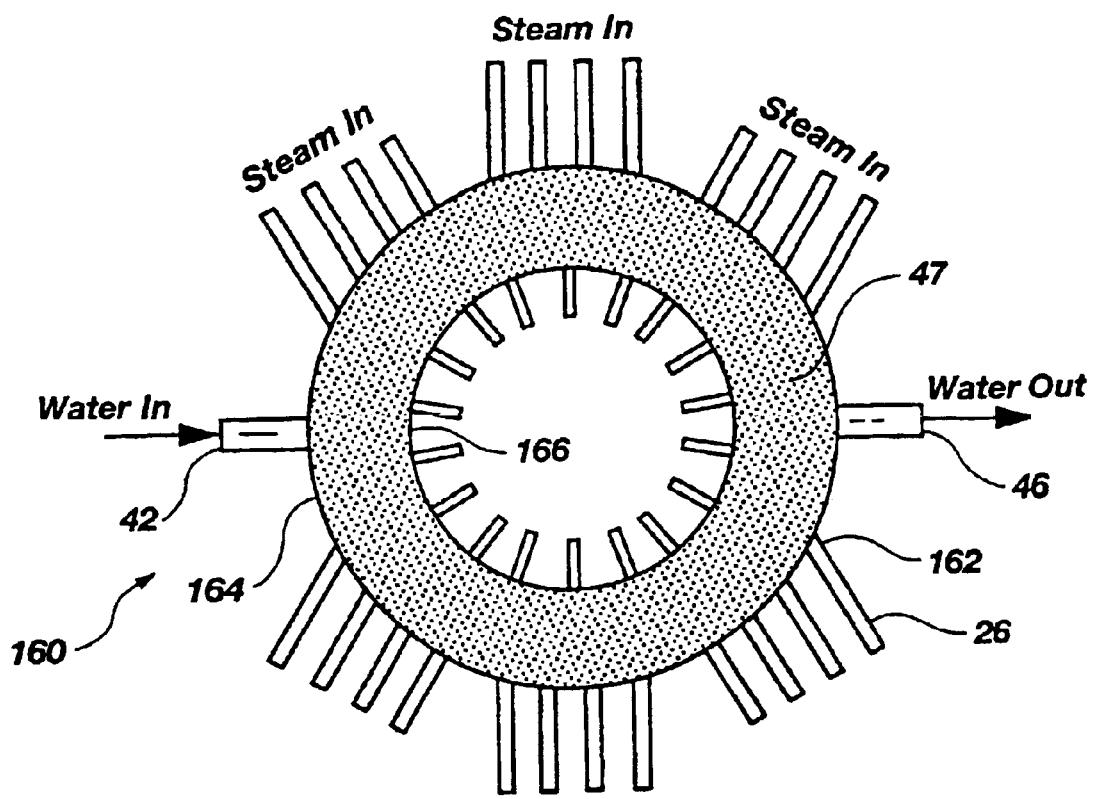
FIG. 10 is a top view of an alternative embodiment of a fluid treatment apparatus in accordance with the principles of the present invention.

Referring to FIGS. 9a and 9b, an apparatus 150 has a vessel 14 with an inner surface forming a sphere A plurality of acoustic sources 152, or nozzle arrays 26, are disposed around the sphere. The acoustic sources 152 have nozzles directed to inject the condensable vapor into the sphere. Because multiple acoustic sources 152 are disposed about the sphere, the acoustic energy or shock waves will converge towards the center of the sphere defining a target zone 56. The acoustic energy may also propagate throughout the sphere. Referring to FIG. 10, an apparatus 160 has a vessel 14 with an inner surface forming a torus, or donut. The fluid inlet 42 and fluid outlet 46 may be disposed on opposing ends of the torus, forming the fluid flow path 47 to split and have one portion flow around one half of the torus and another portion flow around the other half. A plurality of acoustic sources 162, or nozzle arrays 26, are disposed around the torus with some being disposed on the outside 164 of the torus and some being disposed on the inside 166 as shown. The acoustic sources 162 may also be disposed about the circumference of the cross section of the torus, similarly to that of the cylinder in FIGS. 8a and 8b. The torus may have a cross-sectional shape that is right circular. Alternatively, the cross-section of the torus may be elliptical, etc. Furthermore, the cross-section of the torus may be composed of multiple, partial ellipses coupled together, similar to those of FIGS. 4 and 6.

A method for sterilizing water having micro-organisms therein using the apparatuses or system described above includes causing the water to be treated to flow into an elongated vessel. The vessel has an inner surface shaped to focus acoustic energy. Steam is selectively injected by spargers into the vessel at points along the length of the vessel. The steam rapidly condenses in the presence of the water creating acoustic energy. The acoustic energy is focused by reflector members disposed about the spargers to a specific zone within the vessel and extending the length of the vessel defining a target zone. The inner surface of the vessel also focuses and directs the acoustic energy to the target zone.

While the above described and illustrated systems or apparatuses are particularly well suited for use with continuously flowing fluids, and also may be readily adapted for stand alone purposes. For example, situations may occur in which it is difficult or impossible to induce a desired fluid or material to flow into and through the chamber. Such a situation exists with respect to the formation of zebra mussels on screens. While the water surrounding the mussels and the screens is readily induced into a chamber, the mussels are fixed to the screens.

Figure 11:
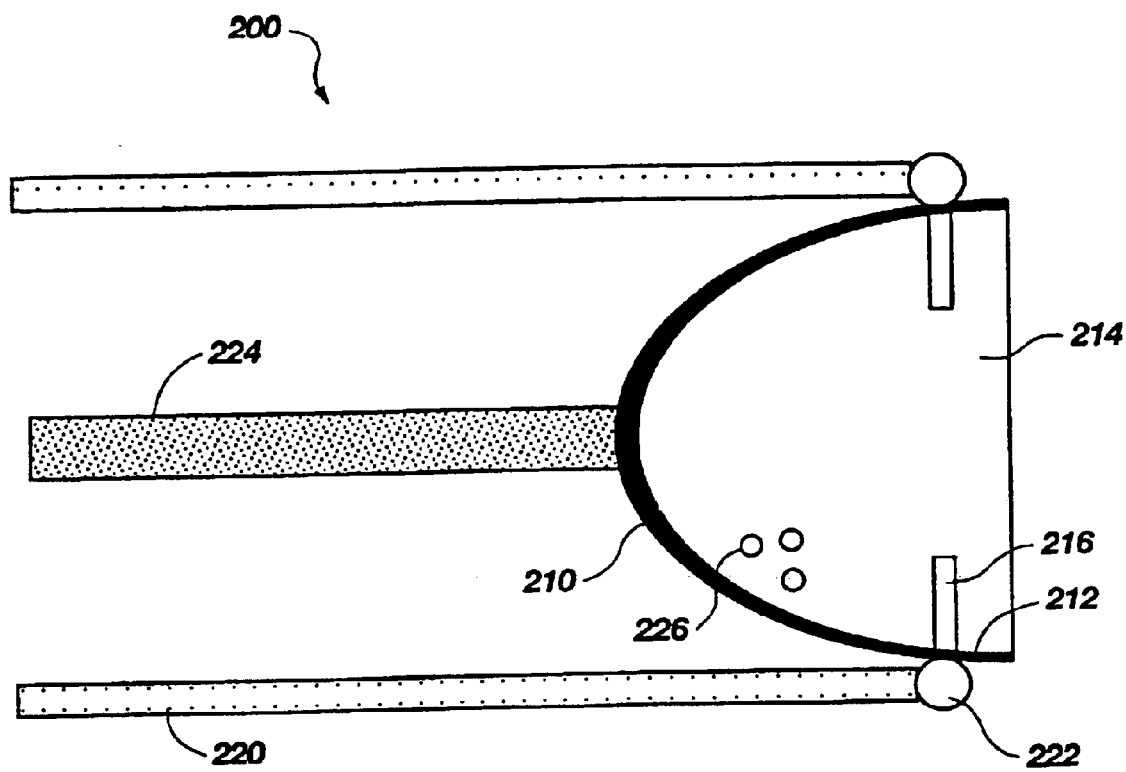
FIG. 11 is a side, cross-sectional view of an alternative embodiment of a water treatment device in accordance with the principles of the present invention.
Figure 12:
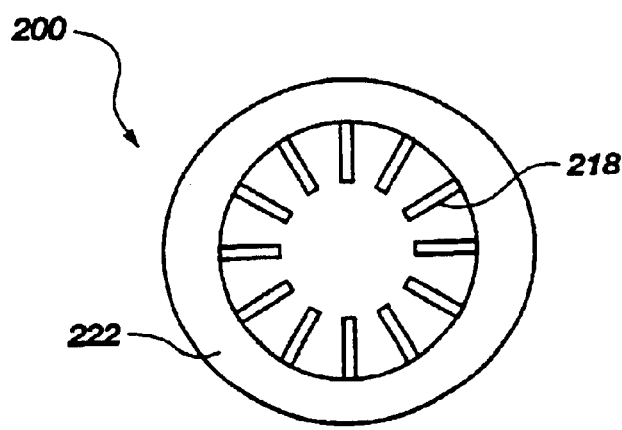
FIG. 12 is an end view of the water treatment device of FIG. 11.

Referring to FIGS. 11 and 12, a device for treating a fluid or material therein with acoustic energy is shown, indicated generally at 200. The device 200 is similar in many respects to the acoustic source in the apparatuses or systems described above, but may be positioned or located independent of a vessel or chamber, such that it may be disposed at a desired location where the liquid or materials are located. The device 200 is analogous to conventional electrically powered loud speakers. In addition, the device may even be portable or moveable such that it may be disposed at will with respect to larger volumes of fluid. Alternatively, the device 200 may be permanently installed in a chamber described above as an acoustic source.

The device 200 has a reflector urface 212 forming an indentation 214. The reflector member 210 is disposed in the fluid to be treated and the fluid fills the indentation 214. A nozzle or sparger 216 is coupled to the reflector member 210 and directed into the indentation 214. The nozzle or sparger 216 may be a nozzle or sparger assembly. In addition, the internal geometry of the nozzle or sparger 216 may be based on either smooth or abrupt area nozzle/sparger designs. However, for choked flow discharge, a nozzle geometry with a smooth area change is anticipated to be the most efficient way of injecting steam into the reflector member.

The nozzle 216 injects a condensable vapor, such as steam, into the is indentation. As discussed above, acoustic energy is generated by the rapid condensation of the vapor as it contacts the fluid. A plurality of nozzles or spargers 218 may be coupled to the reflector member and directed into the indentation, as shown in FIG. 12. A supply line or pipe 220 is coupled to the nozzle 216 or plurality of nozzles 218 for supplying the condensable vapor.

Vapor flowing through the process steam supply lines 220 may be modulated by the partial closing and opening of hydraulic valves upstream of the spargers. Insulating jackets may surround each process line to prevent premature condensation and energy loss. Also, a much larger diameter cylindrical insulating jacket may be wrapped around the entire device 200, with an opening at the cavity of the reflector member.

A ring-shaped pipe 222 may be disposed around the reflector member 210 and coupled between the supply line 220 and the plurality of nozzles 218 to distribute the vapor from the supply line 220 to the nozzles 218. A support member 224 may also be attached to the reflector member 210 to support the reflector member 210 and/or locate and position the reflector member 210. The support member 224 may be hollow and in fluid communication with the cavity 214 for conducting a cooling fluid directly into the cavity. Thus, a cooling fluid, such as water, may be injected directly into the cavity 214 and near the sparger 216. In addition, bypass holes 226 may be formed in the reflector member 210 so that fluid may pass though the holes 226 and thus through the cavity 214. Thus, if the device 200 is submerged in a flowing liquid, the liquid may flow through the reflector member 210 and past the sparger 216 to maintain subcooling inside the cavity 214.

The inner wall or surface 212 of the reflector member 210 may be shaped as desired to direct and/or focus the acoustic energy at a desired target area generally outside of the cavity 214. Preferred reflector shapes include parabolic, conical, and circular shapes. Thus, the reflector member 210 may be located and directed towards a desired area. For example, the device 200, or a plurality of devices, may be fixed at various locations around an intake subject to mussel accumulation. Steam may be supplied to the nozzles 216 and 218 to be injected into the cavity 214. The acoustic energy created by the rapid condensation of the steam is directed by the curved wall 212 of the reflector member 210 at the mussels. Alternatively, the device 210 may be moved as desired to treat a particular area. The wall 212 may be shaped as a parabola, a circle, a cylinder, etc. The device 210 may have a single indentation 214 forming a cup-like indentation, as shown, to focus the acoustic energy. Alternatively, the device may have an elongated indentation, forming a half cylinder, with a plurality of nozzles extending along the length of the indentation to treat a longer or wider area.

Thus, it will be recognized that the device 200 is similar to a single unit of the nozzle array 26 and that the device 200 may be configured as an elongated partial cylinder with a plurality of nozzles to form a nozzle array 26 as an integral part of the vessels described above, or may be used independently.

The above acoustic source emits acoustic pulses that contain a range of differing frequency components. Generally, lower frequency components help to facilitate long range penetration with minimal acoustic dissipation, while high frequency components help to maximize the rate of secondary cavitation in a target zone. In order to optimize this frequency spectrum for a particular application, several other possible design options can be employed to modify this frequency spectrum which include modification to nozzle hole sizes, nozzle positions, using special resonating cavities in the stream lines upstream of the nozzle choke planes and injection points into the liquid cavity, and modifying the nozzle bodies themselves to interact and vibrate with localized imploding vapor cavities. Design modifications to the nozzle bodies may entail adding metal fins or flexible diaphragms to these members to induce high frequency vibrations. In addition, such design modifications must be balanced against the need to minimize local wall cavitation erosion and other forms of material fatigue in and about the vapor implosion zone in the reflector cavity.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

I claim:

1. An apparatus for treating a fluid with acoustic energy, the apparatus comprising:
   a vessel having an inner surface defining a chamber configured for receiving a fluid, the vessel having an inlet and outlet;
   at least one nozzle coupled to the vessel and directed into the chamber, the at least one nozzle configured for injecting a condensable vapor into the chamber to create acoustic energy by rapid condensation of the vapor as it contacts fluid present within the chamber; and
   a structure affixed to the at least one nozzle and configured for at least directing the acoustic energy generated by the rapidly condensing vapor toward a particular zone within the chamber defining a target zone.

2. The apparatus of claim 1, wherein the structure affixed to the at least one nozzle comprises at least one reflector member coupled to the at least one nozzle and having a curved wall defining an indentation for focusing and/or directing the acoustic energy toward the target zone.

3. The apparatus of claim 1, wherein the inner surface of the vessel is shaped to at least direct the acoustic energy toward the target zone.

4. The apparatus of claim 3, wherein the inner surface of the vessel comprises at least two adjoining portions that define a fluid channel with the target zone therein, and wherein each portion has an inner surface which forms a curve to at least direct the acoustic energy toward the target zone.

5. The apparatus of claim 4, wherein the curve formed by the inner surface of each portion is elliptical.

6. The apparatus of claim 4, wherein the curve formed by the inner surface of each portion is parabolic.

7. The apparatus of claim 3, further comprising:
   a first nozzle directed to inject the condensable vapor at a first location within the chamber;
   a second nozzle directed to inject the condensable vapor at a second location within the chamber, the second location separated from the first location;
   wherein the inner surface of the vessel has a first curved portion shaped to direct the acoustic energy generated proximate to the first location toward the target zone, and a second curved portion shaped to direct the acoustic energy generated proximate to the second location toward the target zone, the target zone separated from both the first and second locations.

8. The apparatus of claim 3, wherein the inner surface of the vessel forms an elongated cylinder, and further comprising a plurality of nozzles disposed around a circumference of the inner surface and along the length of the inner surface.

9. The apparatus of claim 3, wherein the inner surface of the vessel is spherical, and further comprising a plurality of nozzles disposed around the inner surface.

10. The apparatus of claim 3, wherein the inner surface of the vessel forms a torus, and further comprising a plurality of nozzles disposed around the inner surface.

11. An apparatus for sterilizing water containing microorganisms by destroying the micro-organisms with acoustic energy, the apparatus comprising:
    a vessel having an inner surface defining a chamber configured for receiving a fluid, the vessel having an inlet and outlet; and
    at least one acoustic source coupled to the vessel and directed into the chamber, the at least one acoustic source having at least one steam sparger coupled to the vessel and directed into the chamber, the at least one acoustic source also having at least one reflector member disposed in the chamber and coupled to the at least one steam sparger, the reflector member having a curved wall defining an indentation for, at least directing the acoustic energy toward a particular zone within the chamber defining a target zone.

12. The apparatus of claim 11, wherein the inner surface of the vessel forms a first elongated portion having a partially elliptical cross section and a second elongated portion parallel with the first portion having a partially elliptical cross section coupled to the second portion, and wherein the at least one acoustic source comprises:

a first steam sparger and a first reflector member, the first steam sparger configured for injecting steam into the first portion generally within the first reflector member the first steam sparger and first reflector member each sized and configured to at least direct the acoustic energy created by the rapid condensation of the steam toward the target zone; and a second steam sparger and a second reflector member, the second steam sparger configured for injecting steam into the second portion generally within the second reflector member the second steam sparger reflector member each sized and configured to at least direct the acoustic energy created by the rapid condensation of the steam toward the target zone.

13. The apparatus of claim 12, wherein the inner surface forms a third elongated portion having a partially elliptical cross section coupled to the first portion and the second portion, the third portion having a third outer focal point; and a third steam sparger with a third reflector member, the third steam sparger configured for injecting steam into the third portion and generally within the third reflector member, the third steam sparger and third reflector member each sized configured to at least direct the acoustic energy created by the rapid condensation of the steam toward the target zone.

14. The apparatus of claim 12, wherein the vessel has a baffles disposed at opposing ends of the vessel sized and configured to inhibit a pressure or cavitation condition.

15. The apparatus of claim 12, wherein the vessel has opposing ends with curved walls sized and configured to inhibit a pressure or cavitation condition.

16. An apparatus for treating a fluid with acoustic energy, the apparatus comprising:

a vessel having an inner wall defining a chamber configured for receiving a fluid, the vessel having an inlet and outlet;

at least one steam sparger coupled to the vessel and directed into chamber, the at least one steam sparger configured for injecting steam into the chamber to create acoustic energy by rapid condensation of the steam as it contacts fluid within the chamber;

a steam drum coupled to the at least one steam sparger by at least one steam supply line extending between the drum and the at least one steam sparger, the steam drum defining an interior cavity configured for receiving steam and equalizing steam pressure to the at least one steam sparger.

17. The apparatus of claim 16, wherein the at least one steam supply line is substantially straight to protect against water hammer damage.

18. The apparatus of claim 16, further comprising a source of steam for providing steam to the steam drum.

19. The apparatus of claim 18, wherein the source of steam utilizes waste heat to provide steam.

20. An apparatus for treating a fluid with acoustic energy, the apparatus comprising:

a vessel having an inner surface defining a chamber configured for receiving a fluid, the vessel having a primary inlet configured for allowing fluid to enter into the chamber and a primary outlet configured for allowing fluid to exit the chamber, the vessel also having a secondary inlet configured for allowing a cooling fluid to enter the chamber; and at least one steam sparger coupled to the vessel and directed into the chamber, the at least one steam sparger configured for injecting steam into the chamber to create acoustic energy by rapid condensation of the steam as it contacts fluid within the chamber.

21. The apparatus of claim 20, further comprising a source of cooling fluid and a delivery structure for introducing the cooling fluid into the vessel.

22. An apparatus for treating a fluid with acoustic energy, the apparatus comprising:

a vessel having an inner surface defining a chamber configured for receiving a fluid, the vessel having an inlet and outlet;

at least one steam sparger coupled to the vessel and directed into chamber, the at least one steam sparger configured for injecting steam into the chamber such that acoustic energy is created by the rapid condensation of the steam as it contacts fluid within the chamber;

a wall heating structure disposed about at least a portion of the vessel for heating the inner surface to biological growth thereon.

23. The apparatus of claim 22, wherein the vessel is a primary vessel, and wherein the wall heating structure comprises a secondary vessel formed about the primary vessel defining a space therebetween configured for receiving steam.

24. The apparatus of claim 22, wherein the wall heating structure comprises a steam pipe coiled around the vessel and configured for receiving steam and transferring heat therein through the steam pipe and vessel to the inner surface.

25. A system for treating a fluid with acoustic energy, the system comprising:

a vessel having an inner wall defining a chamber configured for receiving a fluid, the vessel having a primary inlet configured for allowing fluid to enter into the chamber and a primary outlet configured for allowing fluid to exit the chamber, the vessel also having a secondary inlet configured for allowing a cooling fluid to enter into the chamber;

at least one steam sparger coupled to the vessel and directed into the chamber, the at least one steam sparger configured for injecting steam into the chamber to create acoustic energy by the rapid condensation of the steam as it contacts fluid within the chamber;

a steam drum coupled to the at least one steam sparger by at least one steam supply line extending between the drum and the at least one steam sparger, the steam drum defining an interior cavity configured for receiving steam and equalizing steam pressure to the at least one steam sparger; and a wall heating structure disposed about at least a portion of the vessel for heating the inner surface to inhibit biological growth thereon.

26. The system of claim 25, further comprising a source of cooling fluid and a delivery structure for introducing the cooling fluid into the vessel.

27. The system of claim 25, further comprising a source of steam for providing steam to the steam drum, the steam spargers and the wall heating structure.

28. The system of claim 27, wherein the source of steam utilizes waste heat to provide steam.

29. The system of claim 25, wherein the vessel is a primary vessel, and wherein the wall heating structure comprises a secondary vessel formed about the primary vessel defining a space therebetween configured for receiving steam.

30. The system of claim 25, wherein the wall heating structure comprises a steam pipe coiled around the vessel and configured for receiving steam and transferring heat therein through the steam pipe and vessel to the inner surface.

31. The system of claim 25, wherein the inner surface of the vessel forms a first partially elliptical portion and a second partially elliptical portion coupled to the second portion and wherein the at least one steam sparger comprises:

a first steam sparger coupled to the vessel at the first portion, the first steam sparger configured for injecting steam into the first portion to at least direct the acoustic energy created by the rapid condensation of the steam toward the target zone; and a second steam sparger coupled to the vessel at the second portion, the second steam sparger configured for injecting steam into the second portion to at least direct the acoustic energy created by the rapid condensation of the steam toward the target zone;

wherein the first steam sparger and second steam sparger are sized and configured to caused secondary cavitation in the target zone as the acoustic energy created by the first steam sparger and the second steam sparger interferes in the target zone.

32. A device for treating a fluid with acoustic energy, the device comprising:

a reflector member having a curved wall forming an indentation, the reflector member configured for disposition in a fluid and receiving the fluid within the indentation;

at least one steam sparger coupled to the reflector member and directed into the indentation, the at least one steam sparger configured for injecting steam into the indentation, wherein the curved wall of the reflector member is shaped to at least direct acoustic energy created by rapid condensation of the steam in the presence of the fluid.

33. The device of claim 32, further comprising a delivery structure for injecting a cooling fluid into the indentation of the reflector member.

34. The device of claim 32, further comprising one or more holes formed in the curved wall of the reflector member for allowing the fluid to pass.

35. A method for treating a fluid, the method comprising:

disposing a fluid into a vessel having an inner surface;

selectively injecting steam into the vessel to contact the fluid and rapidly condense the steam to create acoustic energy; and directing the acoustic energy toward a specific zone within the vessel defining a target zone.

36. A method for sterilizing water having microorganisms therein, the method comprising:

causing water to flow into an elongated vessel having an inner surface which is shaped to direct acoustic energy;

selectively injecting steam into the vessel at selected points along the vessel and at specific locations within the vessel such that the steam contacts the water and rapidly condenses to create acoustic energy; and directing the acoustic energy toward a specific zone within the vessel the specific defining a target zone.

* * * * *